US005629350A

United States Patent [19]
Gartner

[11] Patent Number: 5,629,350
[45] Date of Patent: May 13, 1997

[54] SUSPENSION FORMULATIONS OF ORTHO-PHENYLPHENOL

[75] Inventor: Charles D. Gartner, Midland, Mich.

[73] Assignee: The Dow Chemical Company, Midland, Mich.

[21] Appl. No.: 618,883

[22] Filed: Mar. 20, 1996

[51] Int. Cl.$^6$ .................. A01N 25/00; A01N 25/08; A01N 25/30; A01N 31/08
[52] U.S. Cl. ............ 514/736; 514/772; 514/772.1; 514/772.3; 514/773; 514/777; 514/778; 514/779; 514/780; 514/781; 514/782; 514/783
[58] Field of Search ..................... 514/736, 772, 514/777, 778, 779, 780, 781, 782, 772.1, 772.3, 773, 783

[56] References Cited

U.S. PATENT DOCUMENTS

| | | | |
|---|---|---|---|
| 3,948,636 | 4/1976 | Marks | 71/DIG. 1 |
| 3,996,378 | 12/1976 | Payton | 514/516 |
| 4,770,694 | 9/1988 | Iwasaki et al. | 71/DIG. 1 |
| 5,446,014 | 8/1995 | Schuppiser et al. | 504/250 |

FOREIGN PATENT DOCUMENTS

| | | |
|---|---|---|
| 57058601 | 4/1982 | Japan . |
| 9500019 | 5/1995 | WIPO . |

OTHER PUBLICATIONS

*Derwent Publication No.* 88–252006/36, EP 281460, Rhone–Poulenc Chimi, Feb. 23, 1987, Aq. Compsns. Contg. Cationic Organic cpds. — Thickened With Low–Viscosity Xanthan Gum.

*Derwent Publication No.* 89–244059/23, JO 1175–902–A, Kumiai Chem Ind KK, Dec. 28, 1987, Agricultural Suspension Compsn. With Low Viscosity–Contains Sparingly Water–Soluble . . . .

*Derwent Publication No.* 73–54875U–AG, DT–2309983–Q, Akzona Inc., (Jan. 3, 1972) Stable AQ Dispersions of Encapsulated Insecticides, and Pesticides — Using Polysaccharide Gums as . . . .

Nagui I. Ibrahim and Dev K. Mehra, "Colloidal Microcrystalline Cellulose as a Thickener in Flowables", *Pesticide Formulations and Applications Systems*, vol. 12, issue 1146, 1993, pp. 116–132.

Derwent Abstract 40125 E/20, abstracting JP 57–58601 (Apr. 1982).

*Primary Examiner*—John Pak
*Attorney, Agent, or Firm*—Gregory L. Porter; James M. Pelton; Stephen S. Grace

[57] ABSTRACT

Stable, concentrated aqueous suspensions of ortho-phenylphenol (OPP) which contribute minimal chemical oxygen demand and methods of preparing and using said suspensions in biocidal applications have been discovered. The formulations comprise from about 3 to about 70 weight percent of OPP suspended in about 30 to about 97 weight percent water in the presence of a suspending amount of a thixotrope that exhibits Ellis-Plastic behavior.

12 Claims, No Drawings

SUSPENSION FORMULATIONS OF ORTHO-PHENYLPHENOL

FIELD OF THE INVENTION

The present invention concerns stable, concentrated aqueous suspensions of ortho-phenylphenol and methods of preparing and using said suspensions in biocidal applications.

BACKGROUND OF THE INVENTION

Ortho-phenylphenol (OPP) is useful in aqueous systems due to its biocidal activity. OPP has proven especially effective in controlling pathogenic organisms and viruses. As such, OPP is often useful as an active ingredient in disinfectant formulations for homes and hospitals. OPP is often added to metalworking fluids, cosmetics, toiletries and ceramics to control spoilage or decomposition. OPP may also be applied to leather goods to impart mold resistance.

In order to keep shipping costs down, OPP is often sold and shipped in 100 percent active form, i.e., solid form. Unfortunately, handling of solid OPP has disadvantages. One disadvantage is that dust may occur which can be flammable. Another disadvantage is that the solid form is not easily added to an aqueous system via automation due to the difficulty of metering solids. Yet another disadvantage is that the OPP may not be easily dispersible in the aqueous system and vigorous agitation may be required.

For the above reasons, in some applications it may be desirable to employ OPP in a liquid formulation. Usually, OPP is dissolved in a liquid such as an organic solvent or a mixture of organic solvent and water.

Unfortunately, a disadvantage of liquid formulations comprising OPP and organic solvents is that said formulations are fairly expensive due to the cost of the organic solvents. In addition, the formulations have a reduced active concentration and reduced physical stability, i.e., inhomogeneity may result upon freezing and thawing. Yet another disadvantage of liquid OPP formulations which employ organic solvents are the environmental concerns associated with the organic solvents.

One such environmental concern is that increased chemical oxygen demand of the industrial waste water, e.g., cooling tower effluent, results when OPP is employed with organic solvents. Chemical oxygen demand represents the amount of oxygen consumed in the oxidation of organic and oxidizable inorganic material contained in the waste water. See Richard J. Lewis, *Hawley's Condensed Chemical Dictionary,* Twelfth Edition, 1993, p. 253. A high chemical oxygen demand is undesirable for a body of water whether the body be a wastewater treatment pool or a natural body of water.

A high chemical oxygen demand for a body of water is undesirable because biodegradation of microorganisms may cause oxygen depletion in said body of water. If the body of water is a wastewater treatment pool then oxygen depletion could be detrimental to the efficient operation of the wastewater treatment plant. If the body of water is a natural body of water then oxygen depletion could be detrimental to aquatic life which require oxygen for survival.

Formulations comprised of OPP and organic solvents contribute more chemical oxygen demand than if OPP is employed alone or with non-organic solvents because organic solvents serve as a feeding ground for microorganisms by providing nutrients. Therefore, even though the OPP may destroy a majority of the microorganisms before it degrades, a few microorganisms still survive. Those few microoganisms multiply very rapidly in the presence of an organic solvent. Therefore, when OPP-treated waste water containing an organic solvent is released to the environment, or even if it is in a closed system, chemical oxygen demand will increase significantly over time due to the rapidly multiplying microorganisms consuming oxygen in the water.

It would be desirable to discover liquid formulations of OPP that utilize water as a suspending medium. This type of formulation would not only reduce the chemical oxygen demand as compared to formulations which employ organic solvents, but such a formulation would also be less expensive with water replacing the organic solvent. It would also be advantageous if a wide range of OPP concentrations could be usefully employed in the formulations. Furthermore, it would be desirable if the formulations were insensitive to changes in temperature.

SUMMARY OF THE INVENTION

Surprisingly, it has been discovered that novel formulations of OPP can be produced which have a lower chemical oxygen demand than previous formulations. Even more surprisingly, the novel, formulations employ water as a suspending medium and do not require the presence of organic solvents. A wide range of OPP concentrations are useful, i.e., about three weight percent to about 70 weight percent of OPP are possible in formulations of the present invention. The formulations are substantially insensitive to changes in temperature from about 0° to about 60° C.

The formulation comprises a suspension of OPP in conjunction with water and a suspending amount of a thixotrope which exhibits Ellis-Plastic behavior. These thixotropes include natural gums such as xantham gum and locust bean gum, resins such as polyacrylic acid, and mixtures thereof.

The present invention also includes a process of making the above formulations as well as a method of using the above formulations. The process comprises suspending at least about 3, preferably at least about 20, more preferably at least about 50, to at most about 70 weight percent OPP in at least about 30, preferably at least about 40, to at most about 97 weight percent water in the presence of a suspending amount of a thixotrope which exhibits Ellis-Plastic behavior. The above formulations are useful as a method for biological control in an aqueous industrial system in need of such control which comprises contacting the system with an antimicrobially effective amount of the above formulation.

The term "thixotrope exhibiting Ellis-Plastic behavior" refers to compounds or mixtures of compounds which cause a formulation to exhibit the following properties. First, the formulation must form a gel which liquefies when agitated, yet returns to the gel state when it is at rest. Second, in contrast to most liquids which will flow when subjected to any shear stress, i.e., force applied to the liquid, no matter how small the stress, formulations of this invention require some minimum amount of shear stress in order to liquefy the formulation and cause it to flow. This minimum amount of shear stress is called the "yield value" and it varies as the particular thixotrope and its concentration vary. The yield value of the thixotrope must be high enough to suspend particles of OPP in water. This means the yield value must exceed the force of gravity acting on OPP or the OPP will settle to the bottom. In general, the minimum yield value necessary to suspend a spherical particle may be determined by the following equation: minimum yield value=$(4/3)(C_r)(\rho_p-\rho_m)$ wherein $C_r$ represents the radius of the particles to be suspended, $\rho_p$ represents the density of the particles to be suspended, and $\rho_m$ represents the density of the suspending matrix. See, for example, Carbopol™ Bulletin DET-3 from BF Goodrich 3/93. Thus, the yield value will necessarily be higher when larger particles of OPP are employed in the formulation. Thirdly, the thixotrope must cause the formulation to exhibit "shear-thinning" behavior. This means that when the shear stress is above the yield value, the viscosity of the formulation will be reduced as the shear stress increases.

The term "suspending amount" refers to that amount of thixotrope that provides for suspending OPP particles such that less than about 5, preferably less then about 3, percent of OPP settle to the bottom during conventional shipment and storage for about 6–12 months, yet still allows the suspension to be pumped as a liquid upon slight agitation.

The term "antimicrobial" refers to the function of OPP as a biocide, i.e., inhibits the growth of, or kills, microorganisms such as bacteria, molds, yeasts, algae, protozoa, etc.

The term "effective amount" refers to that amount of the antimicrobial formulation of the present invention which will provide for biological control in aqueous systems. The term "biological control" or "biologically controlling" refers to prevention, reduction, or elimination of any adverse consequences such as slime formation, corrosion, odor, etc., in aqueous industrial systems that are directly, indirectly, or otherwise due to the presence and/or growth of microorganisms.

The aqueous systems contemplated for application of the method of the present invention include those aqueous industrial systems susceptible to growth, accumulation, or presence of microorganisms; for example, cooling towers, pulp and paper mills, metalworking fluids, air washers, and the like.

DETAILED DESCRIPTION OF THE INVENTION

Suitable thixotropes for suspending OPP in water according to this invention include those which exhibit Ellis-Plastic behavior. These thixotropes typically exhibit a yield value which exceeds the force of gravity acting on the OPP thereby allowing the OPP to be suspended in water. Useful thixotropes include natural gums such as xantham gum and locust bean gum, resins such as polyacrylic acid, and mixtures thereof. Other thixotropes useful in this invention may be determined by the following test.

TEST FOR DETERMINING SUITABLE THIXOTROPES

1. In a cylindrically shaped vessel, a uniform mixture of the thixotrope to be tested is prepared by admixing a predetermined amount of the thixotrope in a predetermined amount of water to give various predetermined concentrations of the thixotrope in water. A series of mixtures ranging from 0.1 weight percent to 2 weight percent thixotrope in water are thus prepared. To each of these mixtures, a predetermined amount of solid OPP is then added with agitation to prepare a series of formulations containing from 3 to 70 weight percent OPP. Typically, a few minutes of agitation is sufficient to achieve a uniform suspended mixture in the form of a gel for each formulation. However, three hours should pass before Step 2 is undertaken in order that the formulation reaches an equilibrium at which it will exhibit its final thixotropic properties.

2. After three hours have passed, the formulations can now be tested for suitability in the invention. Gentle agitation is applied to the formulations. If little or no flow occurs upon agitation of the formulation then the thixotrope is not suitable for use in the invention. Suitable thixotropes (assuming they exhibit suitable yield value and stability as determined in step three below) should cause the formulation to liquefy and flow upon agitation and return to its gel form almost immediately upon cessation of agitation.

3. The formulation's yield value and stability are tested by storing the suspended gel mixtures at about 40° C. for four weeks. If the formulation has not settled in this time then the thixotrope is suitable for use in the invention. Non-uniformity of the formulation indicates unsuitability of the thixotrope for use in this invention. Non-uniformity is detected by the formation of an appreciably particle free upper liquid layer and/or a dense solid bottom layer. If less than about 5 percent of the solid OPP has settled to the bottom or if less than about 10 volume percent of a substantially particle free upper layer has formed, the thixotrope is acceptable for use in formulations of this invention. The amount of solid OPP at the bottom, if any, can be determined by decanting the formulation to leave only the solid OPP that had settled. The solid OPP is then dried and weighed to determine if more than 5 percent of the total OPP has settled. If more than 5 percent of the OPP is present then the thixotrope is unacceptable. If a particle free upper liquid layer exists then it can be determined if said layer is more than 10 volume percent by dividing the depth of the upper layer by the depth of the total formulation. If the ratio is more than 0.1 (10 percent) then the thixotrope is unacceptable.

Once a thixotrope has been identified as useful in the invention by the above test, the suspending amount of thixotrope necessary must be determined. Typically, this amount will vary depending upon the nature of the thixotrope as well as the amount of OPP and water present. However, in general the amount of thixotrope should not be so much that the suspension becomes too thick to be pumped as a liquid. On the other hand, the amount should be sufficient to suspend and maintain the OPP in water with less than about 5, preferably less than about 3, percent of the OPP settling during conventional shipment and storage of the suspension for about 6–12 months. Generally, the suspending amount is at least about 0.03 weight percent of the total suspension, preferably at least about 0.8, to at most about 4, preferably at most about 2 weight percent of the total suspension. A preferred thixotrope and amount is a mixture of from about 0.05 to about 1.5 weight percent xantham gum and about 0.01 to about 0.5 weight percent locust bean gum.

Advantageously, formulations of this invention may be made which utilize a wide range of OPP concentrations. This allows the utilization of a concentration of OPP that is suitable for a particular application as well as a concentration that is convenient to ship and store. Although the concentration of which the formulation is capable may vary with the particular thixotrope chosen, it is usually from at least about 3, preferably at least about 5 weight percent OPP to at most about 70, preferably at most about 60 weight percent OPP. This is due to the fact that with most thixotropes, if more than about 70 weight percent OPP is employed then the formulation will exhibit a clay-like consistency and not readily disperse when employed in an aqueous system. On the other hand, it is not practical to employ less than about 3 weight percent OPP since the relative concentration of thixotrope to OPP increases to the extent that the chemical oxygen demand of the formulation, based on active OPP, asymptotically increases.

Although it is not required, it is desirable to use small particles of the OPP for ease of dispersing and suspending it in the water. This is due to the fact that the required yield value of the thixotrope will be less, as described above, as well as the fact that the OPP will more rapidly disperse in the water. However, the OPP particles should not be so small that dust is problematic. Generally, OPP particle sizes of from at least about 10, preferably at least about 50 microns to about 200, preferably to about 150 microns in diameter are effective when used with the thixotropes disclosed herein.

Water comprises the remainder of the formulation and functions as the suspending medium in which the OPP is substantially uniformly dispersed. It is not necessary that the water be distilled or purified. Normal water, for example tap, well, or distilled, may be employed in most applications. Typically, water is employed in an amount of from at least about 30, preferably at least about 40, to at most about 97, preferably at most about 95 weight percent of the total formulation.

Although it is not necessary in most instances, when utilizing some suspending agents, for example, polyacrylic acid based thixotropes such as Carbopol EZ-1™, it may be desirable to adjust the pH, i.e., either acidify or basify the formulation, before adding the OPP to the water. See, for example, Carbopol EZ-1™ TDS #203 BF Goodrich 3/94, incorporated herein by reference. The desired pH is typically the lowest pH which allows efficient Ellis-Plastic behavior for the thixotropic mixture. In this manner, a uniform mixture of high yield value will result. Typically, the optimum pH for polyacrylic acid thixotropes is usually from about 5.5 to about 8. If acidifying is necessary, almost any acidifying agent may be used, for example oxalic acid, acetic acid, citric acid, carboxylic acids, and mineral acids such as phosphoric acid, sulfuric acid and hydrochloric may be usefully employed. The type of acid and amount may be varied based upon the particular thixotrope, amount of OPP, and the desired application. Correspondingly, if basifying then almost any basifying agent may be used. Examples are alkali metal and alkaline earth metal hydroxides and carbonates. The type of base and amount may be varied based upon the particular thixotrope, amount of OPP, and the desired application.

Although the ingredients of the formulation may be mixed together in any order, for ease of mixing it is desirable to slowly add the suspending amount of thixotrope to a known amount of tap water while agitating until the thixotrope is well dispersed. When necessary, as described above, pH adjustment of the mixture to the desired pH is then performed. The OPP is then added with agitation. The temperature is conveniently about 25° C. although higher temperatures may cause the thixotrope and the OPP to mix more rapidly with the water, but the temperature should not be so high that the OPP melts.

The formulation of the present invention can optionally have other active or inert ingredients conventionally employed in such types of formulations such as corrosion inhibitors, scale inhibitors, colorants, fragrances, etc.

OPP may be useful by itself in the above suspensions or in admixture with other antimicrobial compounds so long as the total amount of antimicrobial compound, i.e., OPP plus other antimicrobial compounds, is between the amounts specified above for OPP alone, i.e., from about 3 weight percent to about 70 weight percent. Other useful antimicrobial compounds are those which are substantially water insoluble, i.e., less than 2 parts per million of the compound dissolve in 100 parts per million water at 25° C., and non-reactive with water, i.e., less than 5 percent of the soluble fraction of the antimicrobial degrades in water in one month at 25° C. Examples of other antimicrobials which may be useful in conjunction with OPP are carbamic acid, butyl-, 3-iodo-2-propynyl ester also referred to as iodopropynylbutylcarbamate (IPBC); 2,4,4'-trichloro-2'-hydroxydiphenylether (triclosan); tetrachloro isophthalonitrile (thalonil); 1,2-dibromo-2,4-dicyanobutane, 3,4,4'-trichlorocarbanalide (TCC); and methylene bisthiocyanate (MBT).

The formulations of the present invention are useful for many different applications. Among useful applications are as an active ingredient in disinfectant formulations for homes and hospitals; as an additive to metalworking fluids, cosmetics, toiletries and ceramics to control spoilage or decomposition; and as a coating on leather goods to impart mold resistance. Although the concentration of OPP employed varies by concentration, typically a minimum of from about 0.1 percent OPP by weight of the formulation is used for disinfectant formulations; from about 0.05 to about 0.15 percent OPP by weight of diluted concentrate is used for metalworking fluids; from about 0.05 to about 0.5 percent OPP by weight of the formulation is used for cosmetics, toiletries, and ceramics; and from about 1.0 to about 1.5 percent OPP by weight of the leather is used for leather goods.

The present invention is illustrated by the following examples; however, the examples should not be interpreted as a limitation upon the scope of the present invention. All percentages are by weight of total formulation unless otherwise indicated.

EXAMPLE 1

A predetermined amount of suspending agent was slowly added to a predetermined amount of well stirred tap water. Mixing was continued until a uniform mixture was obtained. The solution was held at room temperature for thirty minutes. For the formulations which utilize a polyacrylic acid as a suspending agent, 1 Normal sodium hydroxide (NaOH) was added while mixing to raise the pH to 6. A predetermined amount of OPP was then added while mixing. The percentage of each of the ingredients utilized is exemplified in Table 1.

Carbopol™ represents EZ-1 Carbopol™ Resin (available from BF Goodrich); Xanthan gum represents TICAXAN Xanthan Powder™ (available from TIC Gums); and Locust bean gum represents Locust Bean POR/A TIC Powder™ (available from TIC Gums).

TABLE 1

|  | Antimicrobial & Amount | Suspending Agent & Amount | Amount of water |
| --- | --- | --- | --- |
| Sample 1 | 32.5% OPP | 0.27% Carbopol™ | 67.23% |
| Sample 2 | 34.4% OPP | 1.31% xanthan gum 0.43% locust bean gum | 63.86% |

(1) All amounts in weight percent

The chemical oxygen demand (COD) per part per million (ppm) of active OPP can be calculated for both the suspension formulations of this invention and formulations comprising organic solvents. The suspension formulations of this invention compare very very favorably to formulations comprising organic solvents as illustrated in Table 2.

The chemical oxygen demand calculations for suspension A in Table 2 are based on a suspension comprising 40 weight percent OPP, 1 weight percent Xantham gum, 0.33 weight percent Locust bean gum, and 58.7 weight percent water.

The chemical oxygen demand calculations for suspension B in Table 2 are based on a suspension comprising 40 weight percent OPP, 0.5 weight percent Carbopol™, and 59.5 weight percent water.

The chemical oxygen demand calculations for the organic formulation in Table 2 are based on 40 weight percent OPP and 60 weight percent isopropyl alcohol.

TABLE 2

| Anti-microbial | COD (ppm) | | | |
|---|---|---|---|---|
| | 100% Active Antimicrobial | Suspension A | Suspension B | Organic Formulation (1) |
| OPP | 2.61 | 2.66 | 2.63 | 6.21 |

(1) Organic formulations are for comparison purposes only and not part of the instant invention.

What is claimed is:

1. A process which consists essentially of suspending from about 3 to about 70 weight percent of ortho-phenylphenol in about 30 to about 97 weight percent water in the presence of a suspending amount of a thixotrope that exhibits Ellis-Plastic behavior.

2. The process according to claim 1 which consists essentially of suspending from about 45 to about 55 weight percent of ortho-phenylphenol in from about 45 to about 55 weight percent water in the presence of a suspending amount of a thixotrope that exhibits Ellis-Plastic behavior.

3. The process according to claim 1 which consists essentially of suspending from about 15 to about 25 weight percent of ortho-phenylphenol in from about 75 to about 85 weight percent water in the presence of a suspending amount of a thixotrope that exhibits Ellis-Plastic behavior.

4. The process of claim 1 in which the thixotrope is xantham gum, locust bean gum, polyacrylic acid resin, or mixtures thereof.

5. The process of claim 1 in which the thixotrope is xantham gum, locust bean gum, or mixtures thereof.

6. The process of claim 1 in which the suspending amount of the thixotrope is a mixture of from about 0.05 to about 1.5 weight percent xantham gum and from about 0.01 to about 0.5 weight percent locust bean gum.

7. A formulation which consists essentially of from about 3 to about 70 weight percent of ortho-phenylphenol suspended in about 30 to about 97 weight percent water in the presence of a suspending amount of a thixotrope that exhibits Ellis-Plastic behavior.

8. The formulation according to claim 7 which consists essentially of a suspension of from about 45 to about 55 weight percent of ortho-phenylphenol in from about 45 to about 55 weight percent water in the presence of a suspending amount of a thixotrope that exhibits Ellis-Plastic behavior.

9. The formulation according to claim 7 which consists essentially of a suspension of from about 15 to about 25 weight percent ortho-phenylphenol in about 75 to about 85 weight percent water in the presence of a suspending amount of a thixotrope that exhibits Ellis-Plastic behavior.

10. The formulation of claim 7 in which the thixotrope is xantham gum, locust bean gum, or mixtures thereof.

11. The formulation of claim 7 in which the suspending amount of the thixotrope is a mixture of from about 0.05 to about 1.5 weight percent xantham gum and from about 0.01 to about 0.5 weight percent locust bean gum.

12. A method for biological control in an aqueous industrial system in need of said control which comprises contacting the system with an antimicrobially effective amount of the formulation of claim 7.

* * * * *